(12) United States Patent
Rajasekharan et al.

(10) Patent No.: US 6,277,786 B1
(45) Date of Patent: Aug. 21, 2001

(54) **HERBICIDE COMPRISING PHYTOTOXINS OF *LASIODIPLODIA THEOBROMAE* (LT) FUNGUS, A PROCESS OF PRODUCING THE HERBICIDE AND A METHOD OF USING THE SAME**

(75) Inventors: Ram Rajasekharan; Rosaline Rodrigues; Sairam Reddy, all of Karnataka (IN)

(73) Assignees: Nagarjuna Holding Private Limited, Andhra; Indian Institute of Science, Karnataka, both of (IN)

( * ) Notice: Subject to any disclaimer, the term of this patent is extended or adjusted under 35 U.S.C. 154(b) by 0 days.

(21) Appl. No.: 09/515,479

(22) Filed: Feb. 29, 2000

(51) Int. Cl.[7] .................................................. A01N 63/04

(52) U.S. Cl. ............................................................ 504/117

(58) Field of Search .......................... 504/117; 435/171, 435/254.1, 911

(56) References Cited

PUBLICATIONS

Duke et al. "Herbicides from Natural Compounds". Weed Technology. 1:122–128, 1987.*
Strobel, Gary A. "Biological Control of Weeds". Scientific American. 72–78, Jul. 1991.*

* cited by examiner

*Primary Examiner*—S. Mark Clardy
(74) *Attorney, Agent, or Firm*—Abelman, Frayne & Schwab

(57) ABSTRACT

The invention relates to describe host-specific extracellular phytotoxins produced by *Lasiodiplodia theobromae* (LT, also *Botryodiplodia theobromae*) that has a broad range as a pre-emergent and/or post-emergent bioherbicide, this isolate has been deposited in Microbial Type Culture Collection, Chandigarh, India and given an accession number MTCC 3068, a method using LT-toxin has been developed for controlling certain herbs including *Parthenium hysterophorus*, duckweeds, jimsonweed, black nightshade, prickly sida and *Euphorbia hirta*, these phytotoxins can be used partially pure, as a cell-and spore-free filtrate, a crude filtrate, or a crude suspension of the culture and optionally along with other additives.

27 Claims, 1 Drawing Sheet

A typical HPLC, C18 reverse phase column elution Profile of partially purified LT-Toxin Retention Time + represents a profound phytotoxic effect .

Figure 1. A typical HPLC, C18 reverse phase column elution Profile of partially purified LT-Toxin Retention Time + represents a profound phytotoxic effect.

HERBICIDE COMPRISING PHYTOTOXINS OF *LASIODIPLODIA THEOBROMAE* (LT) FUNGUS, A PROCESS OF PRODUCING THE HERBICIDE AND A METHOD OF USING THE SAME

FIELD OF THE INVENTION

The present invention relates to the biological control of unwanted herbs by the use of a pathogenic toxin from *Lasiodiplodia theobromae* (LT). The invention also provides a novel herbicidal composition, a process for the preparation of the composition and its use in controlling weeds.

BACKGROUND AND DESCRIPTION OF THE PRIOR ART

The Phytotoxins are host-specific because they are toxic only to the host that is, susceptible to the pathogen (which produces the toxin), and if they induce nearly all symptoms of the disease then they are considered to be definitive chemical probes in a study of disease susceptibility and physiological stress at the molecular level (Bottini A. T., and Gilchrist, D. G. 1981. Tetrahedron lett. 22:2719–2722). Physiological, biochemical, genetic and histological data all confirm that these toxic compounds produced by the fungi are the key determinants of disease and host selection (Scheffer, R. P., Kohmoto, K. and Durbin, R. D., 1989. ed. Host-Specific Toxins, pp.1–17).

The tolerance and sensitivity to a toxin is controlled by the same genes in the same way as they control resistance and susceptibility to the fungus (Scheffer, Robert P. and Livingston, Robert S.,1984. Science, 223:17–21). If a fungus does not grow on a plant, the phytotoxin produced by the fungus will not affect that plant, depending on whether or not it has dominant or recessive alleles (Grogan, R. G., Kimble, K. A., and Misaghi, I., 1975. Phytopathology, 65:880–886).

Members of the genus Lasiodiplodia are known to produce a wide range of phytotoxic compounds which affect a large number of plants on which the fungus is found (Domsch, K. H., and Ganms, W., 1980. Compendium of soil fungi, vol.1, Academic press, pp:143–145 ). *Lasiodiplodia theobromae* is a widespread soil-borne saprophyte or wound parasite in the tropics of all continents but has not been reported from the temperate zones of Europe and the U.S.A. It is common on fruits, stems and roots of numerous tropical and subtropical plants, particularly Theobromae, Castilla, Hevea, Citrus, Mangifera, Ficus and Musa (Goss, R. D., Cox, E. A. and Strotzky, 1961. Mycologia, 53:262–277; Laskin, A. I. and Lechevalier, H. A. (EDS) 1973, Handbook of Microbiology, Vol. 3, Microbial Products, CRC Press, Cleveland)

There are many fungi which are pathogenic to weeds because they produce phytotoxins and, therefore, could be used as herbicides (Abbas, H. K., Boyette, C. D., Hoagland, R. E., and Vesonder, R. F., 1991. Weed Sci. 39:673–677. The genus Aternaria is also known to produce a wide range of phytotoxins (Bruce, V. R., Stack, M. E., and Mislivec, P. B., 1984. J. Food Sci. 49:1626–1627. An isolate of *Fusarium moniliforme*, obtained from infected jimsonweed, was found to produce fumonisin phytotoxin.

The applicants in the course of their studies on *Coleus forskohlii* Briq. (Labiate) found that this plant is susceptible to attack by micro-organisms and most of the pathogens attacking the plant have not been identified. The applicants have also found that a fungus *Lasiodiplodia theobromae* which is responsible for the rot disease in coleus plants, releases certain toxins which exhibit phytotoxicity against weeds like Parthenium.

OBJECTS

The main object of this invention is to provide a novel herbicide effective against a wide range of herbs including weeds.

Another object of the invention is to provide a herbicide comprising a phytotoxically effective amount of the toxin produced by *Lasiodiplodia theobromae* together with an additive or a carrier compatible with the said toxin and soil environment.

A further object of the invention is to provide a method for the preparation of the herbicide.

Yet another object is to provide a method for controlling weeds using the toxins produced by *Lasiodiplodia theobromae*.

SUMMARY

In accordance with the foregoing objects, the invention provides a herbicide comprising phytotoxins produced by *Lasiodiplodia theobromae*, optionally, with appropriate carriers and additives. The invention also provides methods for the preparation of the herbicidal composition and methods for control of herbs including weeds in the field.

DETAILED DESCRIPTION OF THE INVENTION

In the present invention, the applicants describe a method for controlling weeds such as *Parthenium hysterophorus*, duckweeds, jimsonweed, black nightshade, *Euphorbia hirta*, prickly sida etc. using a phytotoxic amount of LT-toxin produced by the fungus *Lasiodiplodia theobromae*. The LT-toxin can be applied to the weeds in any suitable form including cultures of *L. theobromae* fungus in any suitable solvent such as water, and culture filtrate. The LT-toxin can be applied as a post-emergent or pre-emergent herbicide.

*Coleus forskohlii* Briq. (Labiatae) is an useful perennial herb growing in many parts of the world including India and in subtropical Himalayan regions. This herb has been used since ancient times for medical treatment in Hindu and Ayurvedic traditional medicine. Screening of extracts of roots of this plant led to the isolation of a group of diterpenoids possessing the basic skeleton of 11-oxo-manoyl oxide (Tandon et al, 1977. Indian J. Chem. 15B, 880), the main constituent of which being forskolin. Forskolin possesses positive inotropic, antihypertensive and adenylate cyclase stimulating activities. Clinical applications of this diterpenoid as a hypertensive, spasmolytic, lipolytic or antithrombotic agent and for the treatment of glaucoma and cardiac insufficiency are studied. (DeSouza et al, 1983. Mol. Res. Reviews, 201). Forskolin is an approved drug for cancer treatment. Reports are available on the isolation of forskolin from the root of *C. forskohlii* and on the in vitro culture of the same (Yanagihara et al, 1998. Plant Med. 54, 200–204). Because of its pharmacological importance (Mersinger et al, 1995, Plant Med. 62, 169–172) farmers have been encouraged to cultivate *C. forskohlii* in large areas. However, this plant is susceptible to attacks by microorganisms causing severe loss to the farmers, and most of the pathogens have not been identified until the date of this patent application is made.

To isolate the phytotoxin, the applicants cultured the fungus *Lasiodiplodia theobromae* in a defined medium for 1 to 7 days and the cell free filtrate was analyzed for phytotoxic activity using leaf disks of Coleus and Cucumber seeds as pre and post-emergents. The cell free filtrate exhibited phytotoxicity. However, the applicants during the course of their research, found that the phytotoxin did not show growth inhibition in E.coli and Saccharomyces cerevisiae cultures.

The pathogen was isolated and identified. Isolation of the causative organism was done by taking the infected tissues and culturing them on a suitable medium. Among the few isolates, only one was observed to cause severe damage when introduced into healthy Coleus plant. The isolated organism was identified as a fungus, Lasiodiplodia theobromae. This pathogen acts by releasing extracellular toxins, which are, hereafter, referred as LT-toxins.

Studies were carried out with the filtrate (free of organisms and spores) which showed inhibitory effect on the root elongation in cucumber seedlings; necrotic effect on C. forskohlii, ground nut and Parthenium in leaf disk and leaf puncture assays; necrosis was also seen in Coleus leaf callus.

This fungal extracellular toxin exhibits phytotoxicity, so field trials were carried out on Parthenium, which showed promising results. These studies suggested that the fungal filtrate (free of live organisms or spores) can be used as a herbicide to eradicate weeds like Parthenium.

L. theobromae can be easily isolated from susceptible Coleus plants exhibiting symptoms of root rot disease by known procedures. Isolates can be grown on potato-dextrose agar and identified based on conidial morphology (Von Arx, J. A., 1981. The genera of fungi sporulating in pure culture, J. Cramer (EDS)., Germany, pp: 206–207). The fungus is characterized with dark brown hyphae, thick walled fruiting bodies, striate and slowly maturing, one septate ellipsoid conidia. To produce LT-toxin, the fungus is cultured on any suitable medium such as potato-dextrose broth, oat meal broth etc., which promotes its growth. Conventional mycology cultures such as Czapek's medium, cornmeal agar or Sabouraud's Agar may also be used. The fungi will grow over wide range of temperatures, generally, between about 20° C. to about 30° C., the preferred temperature being about 24° C. to 28° C. The most preferred pH for the growth of L. theobromae fungi is about 5.6.

Once sufficient growth of the fungus has been obtained, usually in about 6–8 days, the colonies are harvested. Under such cultivation conditions, the fungus is found to produce toxins. As the cultures are dispersed in water, the innoculum is found to contain conidia and mycelium. The phytotoxin produced by the fungus, LT-toxin is purified from the crude filtrate of Lasiodiplodia theobromae and the purified LT-toxin is further used in the herbicidal composition of the invention.

Hence, one embodiment of the invention relates to a novel herbicide useful for controlling and/or eradicating herbs including weeds, said herbicide comprises phytotoxins obtained from a fungus Lasiodiplodia theobromae (LT), and the preferred phytotoxins are in the form of partially purified toxin, cultures of LT fungus, crude filtrate, cell spore or cell-free filtrate or crude suspensions of Lasiodiplodia theobromae and the present herbicide can be mixed with other additives including conventional formulation, solvents and agents.

Another embodiment of the present invention relates to a process for controlling and/or eradicating herbs including weeds, which process comprising: (a) obtaining Lasiodiplodia theobromae fungus from a plant source; (b) culturing the Lasiodiplodia theobromae fungus in a culture medium (synthetic/natural) and (c) separating the phytotoxins from the culture medium and d) applying the phytotoxins on the target herbs or weeds.

Still another embodiment of the present invention relates to a process for producing a herbicidal composition, comprising (a) culturing the Lasiodiplodia theobromae obtained from a plant source in a culture medium for about 6–8 days, (b) separating the phytotoxins from the culture medium by conventional methods, and (c) admixing the phytotoxins with suitable carriers or additives which are compatible with the fungus and soil environment to obtain a herbicidal composition.

One more embodiment of the present invention relates to a method for controlling and/or eradicating herbs including weeds, said method comprising applying the herbicide on herbs by mixing the herbicide in soil or spraying on the herbs.

In practice, it has been found that the crude filtrate as well as the purified LT-toxin are effective in controlling weeds. Therefore, the crude filtrate may be used as such, if desired, in the herbicidal composition, thereby obviating the need for any purification steps. However, formulations of the pure compound (LT-toxin) are definitely the most preferred and suitable.

While liquid cultures may be used as such or dispersed in water and sprayed on the weeds, the seeds or target plants, it is also possible to dry the culture using conventional techniques such as evaporation or filtration, and mix the dry culture with fertilizers or suitable additives or carriers that serve as adherents and are compatible with the soil environment.

The herbicidal compositions of the invention are prepared by dispersing the cultures in suitable medium at an application rate of active agent, preferably ranging from about 0.1 to about 2.0 Kg/hectare. Suitable media include inert solid, powder, or granular, dry materials or liquid materials. Water is a suitable medium for dispersing LT-toxin-containing cultures. The compositions can include non-inert material such as fertilizers, in the range of about 0.0001% to about 99.9% by weight. It is suitable to use formulations of LT-toxin from crude fungal inocula or fractions thereof, such as cell-free filtrates, thereby obviating the need to isolate the pure compound. However, formulations of the pure compound are certainly suitable.

In an alternative embodiment, controlled release of the herbicide may be accomplished by encapsulation with an inert conventional carrier.

The phytotoxic amount (i.e. that amount needed to kill the weed) of LT-toxin in each formulation can be determined easily for each target weed species. A preferred method of applying LT-toxin containing formulations is by spraying post-emergent weeds or by spraying on the soil before the weeds emerge. Other methods of application will be obvious to those skilled in the art and such method comprise mixing the Lasiodiplodia theobromae toxin with fertilizers or other additives and applying on the soils.

It is pertinent to note that the Lasiodiplodia theobromae toxins obtained from the fungus Lasiodiplodia theobromae are selective in expressing their phytotoxic properties. In that, the phytotoxins are in controlling a specific class of herbs or weeds as described herein below.

The invention is described in detail with reference to the following examples and drawings which are provided merely to illustrate some of the embodiments of the invention. Various modifications that may be apparent to those skilled in the art are deemed to fall within the scope of this invention.

BRIEF DESCRIPTION OF THE DRAWING

In the accompanying drawing, FIG. 1 shows a typical HPLC, C18 reverse phase column elution Profile of partially purified LT-Toxin

EXAMPLE 1

*Lasiodiplodia isolate* was obtained from infected *Coleus forskholii* plants exhibiting symptoms of root rot disease. The isolates were grown on the following media and stock cultures of these were maintained at the Indian Institute of Science, Bangalore, India and also deposited in the Microbial Type Culture Collection, Chandigarh, India and given an accession number MTCC 3068. The compositions of various media are:

| Potato Dextrose Agar (PDA): | |
|---|---|
| Potatoes | 200.0 g |
| Dextrose | 20.0 g |
| Agar | 15.0 g |
| Distilled water | 1.0 liter |

Boil diced potatoes in 500.0 ml of water until thoroughly cooked; filter through cheese cloth and add water to the filtrate upon 1.0 liter. Add Agar to the filtrate and dissolve by boiling. Remove from heat and add glucose, adjust pH to 5.6.

| Sabouraud's Agar: | |
|---|---|
| Glucose | 40.0 g |
| Peptone | 10.0 g |
| Agar | 20.0 g |
| Distilled water | 1.0 liter |
| Adjust pH to 6.8 to 7.0 | |
| OatMeal Agar | |
| Powdered Oatmeal | 30.0 g |
| Agar | 20.0 g |
| Distilled water | 1.0 liter |

Wrap Oatmeal flakes in cheesecloth and hang into a beaker containing water, boil and let simmer for 2 hours; squeeze and filter through cloth. Add Agar and dissolve by boiling.

| Czapek's Solution Agar | |
|---|---|
| $K_2HPO_4$ | 1.0 g |
| $NaNO_3$ | 3.0 g |
| KCl | 0.5 g |
| $MgSO_4.7H_2O$ | 0.5 g |
| $FesO_4.7H_2O$ | 0.01 g |
| Sucrose | 30.0 g |
| Agar | 15.0 g |
| Distilled water | 1.0 liter |

The concentration of filtrate obtained after culturing the fungus is designated as "x".

Potato-dextrose broth (PDB) cultures (1 to 7 days old) of isolates were dispersed by homogenization at 24. degree. C. to 28. degree. C. in 50 ml sterilized distilled water. This inoculum contained conidia and mycelium at a propagule density of $1 \times 10^7$ ml$^{-1}$.

LT-toxin was purified from a crude filtrate of *Lasiodiplodia theobromae*, grown on liquid media. Partially pure LT-toxin was used at concentrations of 0.2 mg/ml distilled water; and 0.5 mg/ml of 10% DMSO. dimethyl sulphoxide Crude filtrate was filtered through 0.20 μm Sartorius filters. For the phytotoxin test, cell free filtrate was extracted successively with hexane (300 ml), Chloroform (300 ml) and 60% (v/v) aqueous methanol (300 ml). Phytotoxic compounds were detected both in the chloroform extract and in aqueous methanol fraction. Phytotoxic compounds were isolated by preparative silica-gel column thin layer chromatography (TLC) on silica-gel plates (E.Merck, Darmstadt, West Germany) developed in the solvent system Butanol: Water: Acetic acid [5:3:2 (v/v)]. FIG. 1 depicts a reverse phase elution profile of partially purified LT-Toxin.

Pathogenicity Tests on Parthenium

Parthenium seeds were planted in a commercial potting mixture supplemented with fertilizer (N:P:K 14:14:14). The plants were watered as needed, and the greenhouse temperature was maintained between 28 and 32. degree. C. with 40 to 60% relative humidity. The photoperiod was 14 h. The fungal inoculum was applied using a sprayer to run-off. Control groups received a filtrate of autoclaved potato dextrose extract or distilled water. Parthenium plants were used in these experiments. Following inoculation, plants were incubated on greenhouse benches under conditions as described above. Three replicates of 10 plants each were used for each treatment. The experiment was repeated four times. Symptom development was monitored daily. Heights of Parthenium plants were measured at the beginning and the end of the experiments. Dry weights of plant material above the soil were determined at the end of the experiments after drying for 48 hours at 60. degree. to 70. degree. C. The results are shown in Table 1.

In intact plants, the damage resulting from the crude, cell-free filtrates and partially purified LT-toxin were identical, including visiability of various sizes of necrotic spots on the leaves and stems of the plants. The cell-free filtrate, LT-toxin and crude filtrate affected the growth and dry weight of plant material biomass. The reduction in biomass was 76% and 59% for LT-toxin and cell-free filtrate, respectively. Plant height was reduced by cell-free filtrates and LT-toxin significantly, as compared to control groups. The two *C. cladasporioides* isolates from the same infected plants were neither pathogenic nor did they produce any detectable phytotoxins. They were therefore used as controls for the method.

TABLE 1

Effects of LT-Toxin on the growth of Parthenium weed

| Phytotoxin (Source) | Toxin used (mg) | Plant height (cm) | Dry Wt. Reduction (%) |
|---|---|---|---|
| *L. theobromae* | | | |
| Crude filtrate | 10.0 | 8.7 | 45 |
| Cell free filtrate | 8.2 | 7.2 | 59 |
| Partially purified | 4.0 | 3.6 | 76 |
| *C. cladasporioides* (Control) | *ND | 17.0 | 1 |

*ND = not detected

EXAMPLE 2

An observational trial was conducted to evaluate the bio-efficacy of culture filtrate of *Lasidiplodia theobromae* against herbs including weeds. The trial was laid out in non-crop area infested with the following weeds: *Amaranthus viridus, Axonopus compressus, Cynodon dactylon, Dactyloctenium aegyptium, Digitaria sanguinalis, Euphorbia geniculata, Euphorbia hirta, Panicum repens, Parthenium hysterophorus, Sida cordifolia* and *Trianthema monogyna*.

Twelve plots each of two meter square area were demarcated for the twelve treatments (Table 2). Successive plots were separated by a strip of weeds of 30 cm width which was untreated. All the plots were uniformly infested with weeds, which were under 10 cm in height. Treatments (Table 2) were imposed as post-emergence spray. Low pressure developing hand sprayer was used to spray twice weekly. Volume of spray fluid used was equivalent to 500 liters per hectare.

Qualitative assessments were made twice a week after imposing treatment. Marginal and tip scorching of older, senile leaves of the weed *Parthenium hysterophorus*, was noticed under treatments involving culture filtrate at all rates, commencing from 4th day after spraying. Chlorosis of leaves of the weeds followed by complete scorching of weeds was noticed.

TABLE 2

Effect of toxin on weeds at 25 days after spraying

| Treatments | No. of weeds per 900 cm$^2$ | Dry wt. of weeds (g/900 cm$^2$) |
| --- | --- | --- |
| Weedy check | 26 | 6.6 |
| Filtrate | | |
| X | 24 | 0.5 |
| 2X | 24 | 0.4 |
| 4X | 26 | 0.2 |
| Filtrate:water | | |
| (diluted sample; 1 = X) | | |
| 1:10 | 25 | 0.8 |
| 1:20 | 28 | 1.2 |
| 1:30 | 24 | 1.8 |
| 1:40 | 24 | 2.6 |
| 1:50 | 23 | 3.6 |
| 1:60 | 28 | 3.9 |
| 1:70 | 26 | 4.8 |
| 1:80 | 27 | 5.1 |
| 1:90 | 22 | 5.9 |

Glyphosate @ 1.50 kg a.i./ha was also used as control.
"X" = normal filtrat; "2X" = twice concentrated filtrate and "4X" = 4 times concentrated filtrate.

Table 2 clearly indicates that more the concentration of the filtrate, lesser the dry weight of the plant.

EXAMPLE 3

Excised Parthenium leaves were used to test the, biological activities of crude and cell-and spore-free filtrates. Excised leaves were placed on moistened filter paper inside 9-cm diameter sterile petri plates. The inocula of crude filtrates, cell-and spore-free filtrates, and the phytotoxin standards were applied to the leaves with micropipets. Amounts used were 100 µl to adaxial or abaxial surfaces at concentrations of: (a) 10 g/100 ml distilled water for the crude and cell-free filtrates; (b) 25 mg of partially purified dissolved in 60 ml of 10% DMSO. Ten leaves were used for each treatment. Control leaves received either potato filtrate, distilled water, or 10% (v/v) DMSO. The plates were sealed with paraflim and incubated under continuous or 12 h light (20 uE.m.sup.-2 s.sup.-1). The phytotoxic effects on the treated excised leaves were evaluated visually for damage for 10 days. Crude and cell-free filtrates and LT-toxin caused similar damage to excised leaves, characterized by autolysis diffusing from the point of treatment along the veins adaxially or abaxially to leaves. The result of this test is depicted in Table 3.

TABLE 3

Effects of fungal extracellular metabolites produced by *Lasiodiplodia theobromae* on excised leaves of Parthenium

| Phytotoxin (Source) | Conc. (µg/ml) | Phytotoxicity |
| --- | --- | --- |
| *L. theobromae* | | |
| Crude filtrate | 100 | + |
| Cell free filtrate | 100 | + |
| Partially purified | 0.2 | + |
| DMSO | 10% | − |
| Control (PDB/D.water) | NIL | − |

Ten leaves were used for each treatment. The phytotoxic damages were evaluated visually for 10 days.
− = no phytotoxic effects
+ = phytotoxic effects

EXAMPLE 4

LT-toxin was applied to excised Parthenium leaves to determine a dose-response curve. Primary and secondary leaves from greenhouse-grown 20-day-old Parthenium plants were used in this study. The LT-toxin used in this study was produced and purified in the following manner.

Growth of Cultures

*Lasiodiplodia theobromae* was grown at 24. degree.C. to 28. degree.C. under light in two litre flasks containing 500 ml potato-dextrose broth (PDB). One litre of PDB was prepared by boiling 200 g of potato and to this extract 20 g of dextrose was added, autoclaved for 20 minutes at 15 lbs. pressure. The sterile media was inoculated with 1 ml of a spore suspension containing approximately 150,000 spores per ml, shaken gently, and incubated as a standing cultures for 7 days. The culture filtrates were collected by successive passage through Whatman No.3 filter paper, and a Sartorius membrane filter (0.20 µm)

The culture filtrate which has been passed through the Sartorius membrane filter and unfiltered filtrate gave similar results in LT-toxin bioassays. Sterile uninoculated media and distilled water were used as controls. The sterile filtrates were stored at 4. degree.C. depending on assay or fractionation. LT-toxin preparations stored for 6 months showed no apparent loss in toxicity based upon dilution end-point bioassay. LT-toxin activity in culture filtrates, as expressed by stem and foliar necrosis, was evident when intact seedlings, excised shoots or leaves were allowed to absorb the culture filtrate through their vascular system.

For routine determination of LT-toxin activity, a detached-leaf bioassay was developed. This procedure involved excising a fully expanded leaf with a razor blade by cutting across the petiole base at an oblique angle so that the cut surface of the petiole was in the same plane as the underside of the leaf thus allowing maximum contact of the cut surface with surface upon which the leaf was placed. The LT-toxin preparation was diluted with water to the desired concentration and 2.0 ml of the diluted preparation was applied to a 9.0-cm filter paper disk (Whatman No. 1) on the bottom of a petri dish. The excised leaf was placed cut-surface down on the filter paper after which the petri dish was covered and placed under continuous illumination (lamps at 60 cm) at 24–28. degree.C. Dilution end points of serial 2-fold series of toxin preparations were determined by scoring leaves with 25% or more of the leaf surface showing intervein necrosis after 48 hours of incubation. The rate and degree of symptom development was concentration dependent up to 48 hours after which no further change in symptoms was generally observed. There was some variation in the sensitivity of leaves of different ages.

LT-toxin severity rating were determined visually by assessing the percentage of the leaflet lamina area with necrotic symptoms and is. expressed as the Leaf Sensitivity Index (LSI) with 0=no visible necrosis, 1=1–25% necrosis, 2=26–50% necrosis, 3=51–75% necrosis, and 4=76–100% necrosis. Leaf bioassays were carried out in triplicate. The inhibition of root growth was determined in seedling assays after 5 days by measurement of the root length relative to that of seedlings germinated on water. The percentage of root growth inhibition in seedling assay was rated on a scale from 0 to 4 using the Root Sensitivity Index (RSI) with 0=no inhibition, 1=1–25% inhibition, 2=26–50% inhibition, 3=51–75% inhibition, 4=76–100% inhibition. Seedling assays were performed in triplicate. The result of the assays is set out in Table 4.

TABLE 4

Leaf disk bioassay

| LT-Toxin | Coleus leaf disk | Parthenium leaf disk | Cucumber seedlings |
|---|---|---|---|
| 0.0 | 0 | 0 | 0 |
| 0.5x | 1 | 1 | 1 |
| 1.0x | 2 | 2 | 2 |
| 2.0x | 4 | 4 | 3 |
| 3.0x | 4 | 4 | 4 |
| 4.0x | 4 | 4 | 4 |

Sensitivity to LT-toxin was monitored by leaf disk assay (10 disk/petri dish/plant in triplicates: 10 seedlings/petri dish) and classified according to the percentage of necrosis development numerically rated using the leaf sensitivity index (LSI) and root sensitivity index (RSI) as follows;
0 = no necrosis/inhibition, 1 = 1–25%, 2 = 26–50%, 3 = 51–75%, 4 = 76–100% necrosis/inhibition Purification:

The extraction procedure for LT-toxin was followed as given in Example No. 4. LT-toxin was dialyzed against 5 mM Tris-Cl (pH 6.8) buffer using 12 Kilodalton cut off dialysis bag overnight with continuous stiring at room temperature. The concentrated active buffer was loaded on to the silica column equilibriated with butanol. The active component was eluted using 100 ml of 100% butanol and the 5 ml fractions were collected. The TLC of these fractions in Butanol: Water: Acetic acid [5:3:2 (v/v)] showed the presence of a single spot. The fractions were pooled and concentrated by a flash evaporator and the compound was methylated. The partially purified compound was analyzed on gas chromatogram fitted with mass spectrometry and infra-red spectrometry. High Performance Liquid Chromatography (HPLC) was performed using methanol: water (0–100% gradient for 30 minutes) as solvent system in C18 reverse phase column. A typical HPLC, C18 reverse phase column elution Profile of partially purified LT-Toxin (FIG. 1). LT-toxin (11.5 mg) was dissolved in 75 ml sterile distilled water to yield a 150 µg/ml solution. This stock solution was diluted serially by two with equal amounts distilled water to a concentration of 0.005 microgram per mL. Six leaves were used for each treatment. Control leaves received distilled water. Excised leaves were placed on moistened filter paper inside 9-cm sterile Petri plates. The different concentrations of LT-toxins were applied to the leaves with a 10 microliter micropipette, 4 to 12 times per leaf, depending on its size. The absolute amount of each application was determined. The plates were incubated under 14 hour light (498. mu.E.m.sup.$-2$ s.sup.$-1$) in the growth chamber at 25. degree. C. with 80–85% relative humidity. Observations of phytotoxicity were made at frequent intervals for five days. The results are shown in Table 5.

TABLE 5

Effect of Partially Purified LT-toxin on Parthenium weed

| Phytotoxin concentration (µg/ml) | Phytotoxicity |
|---|---|
| 0 | – |
| 0.10 | – |
| 0.50 | + |
| 1.5 | ++ |
| 6.2 | ++ |
| 12.5 | +++ |
| 25 | +++ |
| 50 | +++ |
| 100 | +++ |
| 150 | +++ |

Six leaves were used for each treatment. Control groups received only distilled water.
– = No phytotoxicity observed
+ = Less than 1/3 of leaf autolyzed
++ = Less than 1/2 of leaf autolyzed
+++ = More than 1/2 of leaf autolyzed

EXAMPLE 5

Nitrogen fixing bacteria were isolated from the root nodules of ground nut, and Rhizobium, Azatobacter sps were collected from Agricultural University, Bangalore. Different concentrations of partially purified LT-toxin (0.1%, 0.5% and 1.0%) was incorporated into the specific medium (liquid as well as solid), and the above said nitrogen fixing bacteria were cultured along with controls. After 32 h of incubation at 37 degree.C growth was measured. *E.coli* and *Saccharomyces cerevisiae* were also cultured on specific medium containing various concentrations of LT-toxin and growth was observed. The results are shown in Table 6.

TABLE 6

Effect of LT-toxin on the growth of nitrogen- fixing bacteria and other microorganisms

| | Duration of incubation (hour) | 0.1% | 0.5% | 1.0% |
| | | (Concentrations) | | |
|---|---|---|---|---|
| Rhizobium sps. | 32 | ++ | ++ | ++ |
| Control (Rhizobium) | 32 | ++ | ++ | ++ |
| Azatobacter sps. | 32 | ++ | ++ | + |
| Control (Azatobacter) | 32 | ++ | ++ | ++ |
| E. coli | 24 | ++ | ++ | ++ |
| Control (E coli) | 32 | ++ | ++ | ++ |
| Saccharomyces cerevisiae | 32 | ++ | + | + |
| Control (Saccharomyoes) | 32 | ++ | ++ | ++ |

Growth was monitored spectrophotometrically
"Control" represent the same organisms but not treated with toxin
+ = <1.0 Optical Density
++ = >1.0 Optical Density Table 6 clearly indicates that the growth of nitrogen fixing bacteria and *E.coli* are not sensitive to the toxin. Similar effect was observed on the growth of yeast at lower concentration. However, there was a significant reduction in the growth of yeast at higher concentration of toxin.

EXAMPLE 6

Twenty-three weeds and cultivated plants from 10 families were used. They ranged in age from seven to ten days old at the time of spraying. Seeds used in these experiments were obtained from commercial companies or collected locally. The number of plants of each cultivar varied between ten to fifty per pot depending on the plant species. Seeds of each cultivar were planted. The experiment was confirmed by repeating twice. One concentration of LT-toxin at 0.2 mg per ml was prepared in 50 ml distilled water. Cell free filtrate of fungus was prepared by homogenizing 20 g in 100 ml distilled water and filtering through a double layer of cheese cloth. A sprayer was used to apply the LT-toxin solutions until run off. Plants were kept in the greenhouse under the same conditions as described in earlier. Symptoms were observed daily until the end (two weeks) of the experiment and included chlorosis, necrosis, stunting and mortality. The results are shown in Table 7.

TABLE 7

Response of various crop and weed species tested for susceptibility to LT-toxin

| FAMILY<br>Common name, scientific name | young<br>leaves | mature<br>leaves |
|---|---|---|
| POACEAE | | |
| Axonopus compressus | + | I |
| Cyanodondactylon | + | I |
| Dactylocenium aegyptium | + | I |
| Digitaria sanguinalis | + | I |
| Panicum repens | + | I |
| LEMNACEAE | | |
| Common duckweed (*Lemna minor* L.) | ++++ | +++ |
| Duckweed (L.) (*Lemna pausicostata*) | ++++ | +++ |
| MALVACEAE | | |
| Sida cordifolia | ++ | + |
| Prickly sida (*Sida spinosa* L.) | ++ | + |
| SOLANACAEA | | |
| Jimsonweed (*Datura stramonium* L.) | ++ | + |
| AMARANTHACEAE | | |
| Amaranthus viridis | + | I |
| CONVOLVULAVEAE | | |
| Morningglory (*Ipomoea wrightii* Gray) | I | I |
| CUCURBITACEAE | | |
| Cucumber (*Cucumis sativus* L.) | ++++ | +++ |
| ASTERACEAE | | |
| Parthenium hysterophorus | ++++ | ++++ |
| Synedrella | ++++ | +++ |
| Tridax procumbensus | ++++ | +++ |
| EUPHORBIACEAE | | |
| Euphorbia hirta | ++++ | +++ |
| LEGUMINACEAE | | |
| Alfalfa (*Medicago sativa*) | +++ | + |
| Crimson clover (*Trifolium incarnatum* L.) | +++ | + |
| American jointvetch (*Aeschynomene americna* L.) | + | + |
| Indian jointvetch (*Aeschynomene indica* L.) | ++ | + |

+ = 1/4$^{th}$ of leaf disk necrosis
++ = 1/2 of leaf disk necrosis
+++ = 3/4$^{th}$ of leaf disk necrosis
++++ = Complete necrosis
I = immune.

Table 7 clearly indicates that the LT toxin is selective in expressing phytotoxic properties.

What is claimed is:

1. A novel herbicide useful for controlling and/or eradicating herbs including weeds, said herbicide is a phytotoxin obtained from a fungus *Lasiodiplodia theobromae* (LT).

2. A herbicide as claimed in claim 1 wherein the phytotoxins comprise partially purified toxin, cultures of LT fungus, crude filtrate, cell spore or cell-free filtrate or crude suspensions of *Lasiodiplodia theobromae*.

3. A herbicide as claimed in claim 1 comprising other additives including conventional formulation, solvents and agents.

4. A herbicide as claimed in claim 1 wherein the fungus *Lasiodiplodia theobromae* is obtained from a plant source selected from *Coleus forskohlii*, Theobromae, Castilla, Hevea, Citrus, Mangifera, Ficus and Musa.

5. A herbicide as claimed in claim 1 which is useful for controlling the herbs selected from the group comprising *Lemna minor* L., *Lemna pausicostata*, *Sida cordifolia*, *Sida spinosa* L., *Datura Stramonium*, *Cucumis sativus* L., *Parathenium hysterophorus*, *Synedrella*, *Tridax procumbensus*, *Euphorbia hirta*, *Medicago sativa*, *Trifolium incamatum* L. and *Aeschynomene indica*.

6. A process for producing a herbicide according to claim 1, for controlling and/or eradicating herbs including weeds, said process comprising the steps of: (a) obtaining *Lasiodiplodia theobromae* fungus from a plant source; (b) culturing the *Lasiodiplodia theobromae* fungus in a culture medium (synthetic/natural) and (c) separating the phytotoxins from the culture medium.

7. A process as claimed in claim 6 wherein the plant source is selected from *Coleus forskohlii*, Theobromae, Castilla, Hevea, Citrus, Mangifera, Ficus and Musa.

8. A process as claimed in claim 6 wherein the culture medium is selected from potato-dextrose broth culture, oatmeal agar, *Czapek's solution agar* and *Sabouraud's Agar*.

9. A process as claimed in claim 6 wherein the step of separation is performed by centrifugation or filtration.

10. A process as claimed in claim 6 wherein the phytotoxins are effective against herbs selected from *Lemna minor* L., *Lemna pausicostata*, *Sida cordifolia*, *Sida spinosa* L., *Datura Stramonium*, *Cucumis sativus* L., *Parathenium hysterophorus*, Synedrella, *Tridax procumbensus*, *Euphorbia hirta*, *Medicago sativa*, *Trifolium incarnatum* L. and *Aeschynomene indica*.

11. A novel herbicidal composition useful for controlling and/or eradicating herbs including weeds, comprising an effective amount of phytotoxins obtained from *Lasiodiplodia theobromae* fungus (LT), together with a carrier compatible with said fungus and soil environment.

12. A herbicidal composition as claimed in claim 11 wherein the composition is used to control herbs selected from the group comprising of *Lemna minor* L., *Lemna pausicostata*, *Sida cordifolia*, *Sida spinosa* L., *Datura Stramonium*, *Cucumis sativus* L., *Parathenium hysterophorus*, Synedrella, *Tridax procumbensus*, *Euphorbia hirta*, *Medicago sativa*, *Trifolium incamatum* L. and *Aeschynomene indica*.

13. A method for producing a herbicidal composition, said method comprising (a) culturing the *Lasiodiplodia theobromae* obtained from a plant source in a culture medium for about 6–8 days, (b) separating the phytotoxins from the culture medium by conventional methods, and (c) admixing the phytotoxins with suitable carriers or additives which are compatible with the fungus and soil environment to obtain a herbicidal composition.

14. A method as claimed in claim 13 wherein the plant source is selected from plants infected with *Lasiodiplodia theobromae* (LT) comprising: *Coleus forskohlii*, Theobromae, Castilla, Hevea, Citrus, Mangifera, Ficus and Musa.

15. A method as claimed in claim 13 wherein the culture medium is selected from the group comprising Potato-dextrose broth culture, Oat Meal Agar, *Czapek's Solution Agar* and *Sabouraud's Agar*.

16. A method as claimed in claim 13 wherein the phytotoxins are separated from the culture medium by centrifugation or filtration.

17. A method as claimed in claim 13 wherein the phytotoxins are obtained from cell free filtrate, crude filtrate, cell and spore free filtrate or crude suspensions of *Lasiodiplodia theobromae*.

18. A method as claimed in claim 13 further comprising admixing the phytotoxins with water, soil, fertilizers or any appropriate carriers.

19. A method as claimed in claim 13 wherein the phytotoxins are mixed with soil or any carrier in a ratio of 1:100.

20. A method as claimed in claim 13 wherein the phytotoxins are mixed with soil or carriers at a ratio of 1:10.

21. A method for controlling and/or eradicating herbs including weeds, said method comprising applying the herbicide as defined in claim 1 on herbs by mixing the herbicide in soil or spraying on the herbs.

22. A method as claimed in claim 21 wherein the herbs are selected from the group comprising *Lemna minor L., Lemna pausicostata, Sida cordifolia, Sida spinosa L., Datura Stramonium, Cucumis sativus L., Parathenium hysterophorus*, Synedrella, *Tridax procumbensus, Euphorbia hirta, Medicago sativa, Trifolium incarnatum L.* and *Aeschynomene indica*.

23. A method as claimed in claim 21 wherein the crude extract is dried and the dried material is mixed with soil with or without the presence of other additives or added with sufficient quantity of water and/or with any suitable formulation and applied on the soil or foliage of the herbs.

24. A method as claimed in claim 21 wherein the dried material is mixed with water, soil or any suitable additives/formulation in a ratio of 1:100.

25. A method as claimed in claim 21 wherein the dried material is mixed with water, soil or any suitable formulation in a ratio of 1:10.

26. A method as claimed in claim 23 wherein the additives can be fertilizers.

27. A method as claimed in claim 21 wherein the method is selective in nature since the LT toxin is selective in expressing phytotoxic properties.

* * * * *